(12) United States Patent
Prestwich et al.

(10) Patent No.: US 8,859,760 B2
(45) Date of Patent: *Oct. 14, 2014

(54) COMPOSITIONS FOR KILLING OR PREVENTING THE GROWTH OF MICROBES

(71) Applicant: Frontier Scientific, Inc., Logan, UT (US)

(72) Inventors: Glenn Prestwich, Eastsound, WA (US); Jerry C. Bommer, Franklin, ID (US); Charles Testa, Salt Lake City, UT (US)

(73) Assignee: Frontier Scientific, Inc., Logan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/104,098

(22) Filed: Dec. 12, 2013

(65) Prior Publication Data

US 2014/0179742 A1    Jun. 26, 2014

Related U.S. Application Data

(63) Continuation of application No. 13/056,441, filed as application No. PCT/US2009/052128 on Jul. 29, 2009, now Pat. No. 8,633,311.

(60) Provisional application No. 61/084,403, filed on Jul. 29, 2008.

(51) Int. Cl.
*A61K 31/409* (2006.01)
*A61K 31/155* (2006.01)
(Continued)

(52) U.S. Cl.
CPC .............. *A61K 31/444* (2013.01); *A61K 31/155* (2013.01); *A61K 31/4025* (2013.01); *A61K 31/045* (2013.01); *A01N 31/02* (2013.01); *A01N 43/36* (2013.01); *A01N 35/04* (2013.01); *A01N 43/90* (2013.01); *A61K 31/12* (2013.01); *A01N 47/44* (2013.01)
USPC ........... 540/145; 514/333; 514/185; 514/338; 514/410; 424/9.362; 424/9.61; 422/23; 604/20

(58) Field of Classification Search
CPC . A01N 43/90; A61K 41/0071; A61K 30/409; C07D 487/22
USPC .................... 604/20; 514/333, 185, 410, 338; 424/9.61, 9.362; 422/23; 540/145
See application file for complete search history.

(56) References Cited

U.S. PATENT DOCUMENTS 6,066,628 A    5/2000  Stojiljkovic et al.
6,391,323 B1   5/2002  Carnevali
(Continued)

FOREIGN PATENT DOCUMENTS

WO    9300815    1/1993
WO    0147932    7/2001
(Continued)

OTHER PUBLICATIONS

International Search Report dated Dec. 17, 2009 for International Application No. PCT/US2009/052128.
(Continued)

*Primary Examiner* — Savitha Rao
(74) *Attorney, Agent, or Firm* — Gardner Groff Greenwald & Villanueva, P.C.

(57) ABSTRACT

Described herein are methods and compositions for killing or preventing the growth of microbes. It has been discovered that a class of porphyrins can kill or prevent the growth of microbes. The porphyrins can be used in a number of different applications where microbes grow.

13 Claims, 5 Drawing Sheets

(51) Int. Cl.

| | |
|---|---|
| A61K 31/4025 | (2006.01) |
| A61K 31/045 | (2006.01) |
| A01N 31/02 | (2006.01) |
| A01N 43/36 | (2006.01) |
| A61K 31/444 | (2006.01) |
| A01N 35/04 | (2006.01) |
| A01N 43/90 | (2006.01) |
| A61K 31/12 | (2006.01) |
| A01N 47/44 | (2006.01) |

(56) References Cited

U.S. PATENT DOCUMENTS

| | | |
|---|---|---|
| 6,462,070 B1 | 10/2002 | Hasan et al. |
| 6,573,258 B2 | 6/2003 | Boomer et al. |
| 6,610,298 B2 | 8/2003 | Hasan et al. |
| 6,716,794 B2 | 4/2004 | Schaffer et al. |
| 6,884,797 B2 | 4/2005 | Hofmann |
| 7,244,841 B2 | 7/2007 | Love et al. |
| 7,268,155 B2 | 9/2007 | Hasan et al. |
| 2002/0122805 A1 | 9/2002 | Hasan et al. |
| 2002/0183245 A1 | 12/2002 | Hasan et al. |
| 2003/0050296 A1 | 3/2003 | Bommer et al. |
| 2003/0153546 A1 | 8/2003 | Schaffer et al. |
| 2003/0224002 A1 | 12/2003 | Hasan et al. |
| 2004/0143001 A1 | 7/2004 | Love et al. |
| 2004/0245183 A1 | 12/2004 | Jori |
| 2005/0090428 A1 | 4/2005 | Compans et al. |
| 2006/0241095 A1 | 10/2006 | Meunier et al. |
| 2006/0258635 A1 | 11/2006 | Smijs et al. |
| 2007/0167619 A1 | 7/2007 | Love et al. |
| 2007/0281915 A1 | 12/2007 | Love et al. |
| 2008/0015189 A1 | 1/2008 | Hamblin et al. |
| 2008/0031960 A1 | 2/2008 | Wilson et al. |
| 2008/0050448 A1 | 2/2008 | Wilson et al. |
| 2008/0118578 A1 | 5/2008 | Dees et al. |
| 2008/0255498 A1 | 10/2008 | Houle |
| 2009/0275751 A1 | 11/2009 | Nagato et al. |

FOREIGN PATENT DOCUMENTS

| | | |
|---|---|---|
| WO | 02002153 | 10/2002 |
| WO | 03002077 | 1/2003 |
| WO | 03026646 | 4/2003 |
| WO | 2004080174 | 9/2004 |

OTHER PUBLICATIONS

Magaraggia et al., "Treatment of Microbiologically Polluted Aquaculture Waters by a Novel Photochemical Technique of Potentially Low Enviormental Impact", Journal of Environmental Monitoring vol. 8, pp. 923-931, 2006, The Royal Society of Chemistry, Italy.

Kasaab et al., "Photosensitization of *Colpoda inflata* Cysts by Meso-Subsituted Cationic Porphyrins", Photochem. Photobiol. Science, vol. 1, pp. 560-564, 2002, The Royal Society of Chemistry and Owner Societies, Egypt.

Bristow et al., "Potential of Cationic Porphyrins for Photodynamic Treatment of Cutaneous Leishmaniasis", Photodiagnosis and Photodynamic Therapy, vol. 3, pp. 162-167, 2006, Elsevier B.V., United Kingdom.

Hiraga et al. "Antifungal Activities of Novel Light Sensitive Meso-Substituted Cationic Porphyrins", 43rd ICAAC, 2003.

First Examination report for Indian patent application No. 341/MUMNP/2011 dated Jul. 8, 2013.

Office Action for Mexican patent application No. MX/a2011/001005 dated Jun. 25, 2012.

Malik et al, "Photodynamic inactivation of Gram-negative bacteria: problems and possible solutions", Photochem Photobio B Biol, 1992, V 14, p. 262-266.

FIGURE 1
[PBS_treated_72 hrs]
[10% formic acid_72 hrs eschar formation]
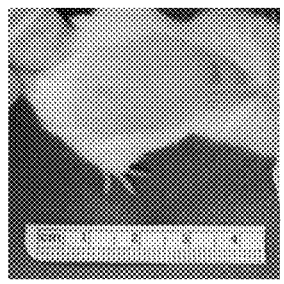
[3 µM LMP_72 hrs]
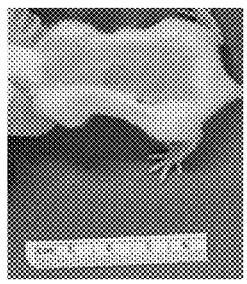
[30 µM LMP_72 hrs]
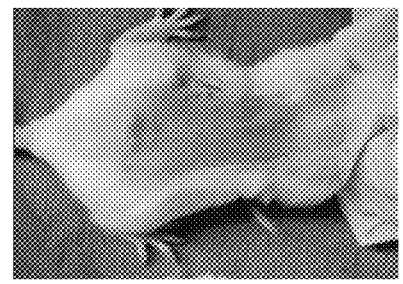
[300 µM LMP_72 hrs]
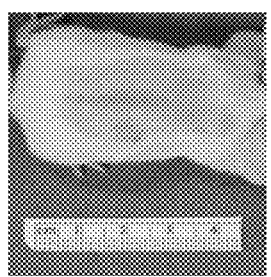
[3µM TMP_72 hrs]
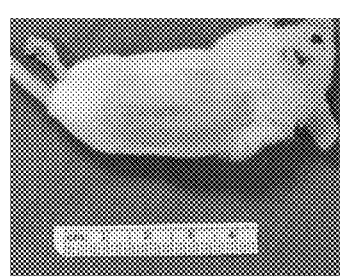
[30 µM TMP_72 hrs]
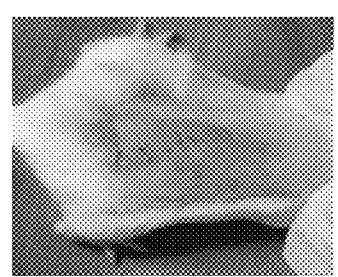
[300 µM TMP_72 hrs]

COMPOSITIONS FOR KILLING OR PREVENTING THE GROWTH OF MICROBES

CROSS REFERENCE TO RELATED APPLICATIONS

This application is a continuation application of U.S. application Ser. No. 13/056,441, filed on Apr. 11, 2011, which is a U.S. national phase application under 35 USC 371 of international application number PCT/US2009/052128, filed Jul. 29, 2009, which claims priority to U.S. provisional application Ser. No. 61/084,403, filed Jul. 29, 2008, which are hereby incorporated herein by reference in their entirety for all purposes.

BACKGROUND

The use of antimicrobial agents to kill or prevent the growth of undesirable organisms has been studied extensively. In particular, antimicrobial agents such as fungicides, antiviral, and antibacterial compounds have been examined. Although a number of antimicrobial agents are effective, they have drawbacks. For example, they can be very toxic and difficult to handle and not environmentally friendly, which limits their use. Thus, it would be desirable to have an antimicrobial agent that can be used in a number of different applications such as, for example, aquatic applications, crop protection, and the treatment or prevention of certain diseases caused by microbes. Described herein are methods and compositions that address the shortcomings of current antimicrobial agents.

SUMMARY

Described herein are articles, compositions, and methods for killing or preventing the growth of microbes. It has been discovered that a class of porphyrins can kill or prevent the growth of microbes. The porphyrins can be used in a number of different applications where microbes grow. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIG. 1 shows gross pictures of mice treated with different concentrations of lauryl methyl pyrifrin (LMP) and TMP.

DETAILED DESCRIPTION

Figure 2:
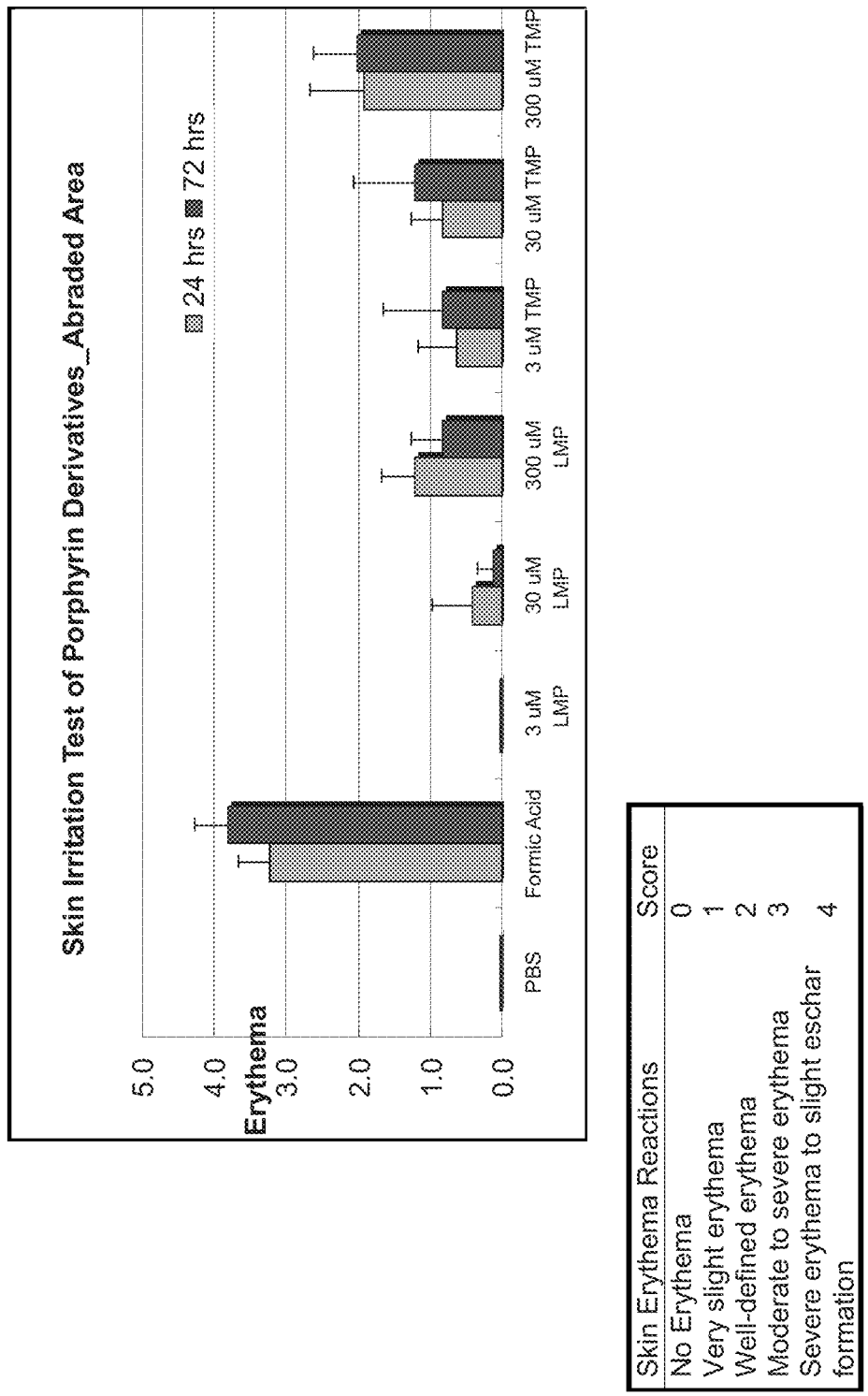
FIG. 2 shows erythema scoring of lauryl methyl pyrifrin (LMP) and TMP porphyrin in an abraded area of mice.

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a microbe" includes mixtures of two or more such organisms, and the like.

"Optional" or "optionally" means that the subsequently described event or circumstance can or cannot occur, and that the description includes instances where the event or circumstance occurs and instances where it does not. For example, the phrase "optionally second disinfectant" means that the second disinfectant may or may not be present.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Variables such as $R^1$-$R^4$ and X used throughout the application are the same variables as previously defined unless stated to the contrary.

The term "alkyl group" as used herein is a branched or unbranched saturated hydrocarbon group having 1 to 14 carbon atoms.

Described herein are methods for killing or preventing the growth of microbes. In one aspect, a method for killing a microbe includes the step of contacting the microbe with a porphyrin having the formula I below

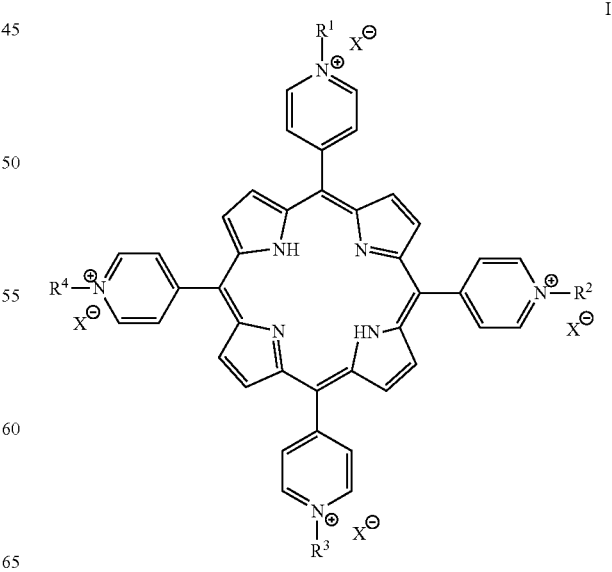

wherein $R^1$-$R^4$ are a $C_1$ to $C_{14}$ alkyl group, and $X^-$ is an anion.

The porphyrins having the formula I can be prepared using techniques known in the art. For example, U.S. Pat. No. 6,573,258 discloses techniques for preparing the porphyrins described herein, which are incorporated by reference. In one aspect, $R^1$ is a $C_{10}$ to $C_{14}$ alkyl group, $R^2$-$R^4$ are, independently, methyl, ethyl, or propyl, and $X^-$ is an anion to produce a porphyrin-treated organism. In another aspect, $R^1$ in formula I is a $C_{10}$, $C_{11}$, $C_{12}$, $C_{13}$, or $C_{14}$ straight chain branched or straight alkyl group. As shown below in the Examples, the length of the alkyl group can affect the ability of the porphyrin to kill or prevent the growth of microbes. In one aspect, $R^2$-$R^4$ are each methyl, ethyl, or propyl. In another aspect, $R^1$ is a $C_{12}$ linear alkyl group and $R^2$-$R^4$ are each a methyl group. In one aspect, X is a halide, sulfate, acetate, lactate, nitrate, phosphate, carbonate, bicarbonate, or tosylate. The identity of the counterion can vary depending upon how the porphyrin was synthesized. For example, if the porphyrin was alkylated with methyl iodide, the counterion would be iodide. It is also possible using techniques known in the art to exchange the counterion of the porphyrin with other counterions. For example, ion exchange resins can be used to replace one counterion for another in the porphyrin.

In certain aspects, the porphyrins herein can kill up to 100% of the microbe. In other aspects, the porphyrins herein can prevent the growth of the microbe. The term "prevent" as used herein includes complete cessation of growth or a reduction with the rate of growth. In general, the porphyrins described herein can kill or prevent the growth of a microbe in any environment where the organisms can exist.

The porphyrins can kill or prevent the growth of a variety of different microbes. In certain aspects, the microbes can be pathogenic and cause debilitating diseases to humans, livestock, and crops. In other aspects, the microbes can produce unpleasant odors. Thus, the articles, compositions, and methods described herein can be used as deodorants as well. For example, the articles and compositions can kill or prevent the growth of bacterium such as, for example *corynebacteria* and *micrococci*, bacteria that cause unpleasant odors.

In one aspect, the articles and compositions can kill or prevent the growth of bacterium such as, for example, gram positive bacteria, gram negative bacteria, or a combination thereof. In one aspect, the bacteria is from the genus *Pseudomonas, Klebsiella, Aerobacter, Burkholderia, Enterococcus, Staphylococcus, Acinetobacter, Flavimonas, Enterobacter, Candida, Bacillus, Streptococcus, Yersinia, Escherichia, Salmonella, Francisella, Haemophilus, Stenotrophomonas, Citrobacter, Proteus, Moraxella, Serratia, Neisseria, Brucella, Clostridium, Chlamydia* or any combination thereof. Examples of such bacteria include, but are not limited to, *Staphylococcus aureus*, oxacillin-resistant *Staphylococcus aureus*, methicillin-resistant *Staphylococcus aureus, Burkholderia cepacia, Burkholderia mallei, Burkholderia pseudomallei, Acinetobacter baumannii, Pseudomonas, aeruginosa, Pseudomonas fluorescens, Flavimonas, Klebsiella pneumoniae, Enterobacter cloacae, Candida albicans, Enterococcus faecalis*, vancomycin-resistant *Enterococcus, Streptococcus pneumoniae, Yersinia pestis, Escherichia coli, Salmonella typhi, Salmonella typhimurium, Francisella tularensis, Haemophilus influenzae, Stenotrophomonas maltophilia, Citrobacter freundii, Proteus mirabilis, Moraxella catarrhalis, Serratia marcescens, Neisseria meningitides, Neisseria gonorrhoeae, Brucella suis, Clostridium difficile, Clostridium botulinum, Chlamydia trachomatis*, or any combination thereof.

In one aspect, the microbe is a fungus, a protozoan parasite, or a parasitic worm. As discussed above, different types of microbes can adversely affect different organisms (e.g., plants, aquatic animals, humans, etc.) or environments. In one aspect, the fungus is an organism from the genus *Candida, Aspergillus, Cryptococcus, Histoplasma, Pneumocystis*, or *Stachybotrys*. Examples of such fungi include, but are not limited to, *Candida albicans, Candida ascalaphidarum, Candida amphixiae, Candida antarctica, Candida atlantica, Candida atmosphaerica, Candida blattae, Candida carpophila, Candida cerambycidarum, Candida chauliodes, Candida corydalis, Candida dosseyi, Candida dubliniensis, Candida ergatensis, Candida fructus, Candida glabrata, Candida fermentati, Candida guilliermondii, Candida haemulonii, Candida insectamens, Candida insectorum, Candida intermedia, Candida jeffresii, Candida kefyr, Candida krusei, Candida lusitaniae, Candida lyxosophila, Candida maltosa, Candida membranifaciens, Candida milleri, Candida oleophila, Candida oregonensis, Candida parapsilosis, Candida quercitrusa, Candida sake, Candida shehatea, Candida temnochilae, Candida tenuis, Candida tropicalis, Candida tsuchiyae, Candida sinolaborantium, Candida sojae, Candida viswanathii, Candida utilis, Aspergillus fumigatus, Aspergillus flavus., Aspergillus clavatus, Cryptococcus neoformans, Cryptococcus neoformans, Cryptococcus gattii, Histoplasma capsulatum, Pneumocystis jirovecii, Stachybotrys chartarum*. These microbes can produce a variety of different symptoms and diseases including, but not limited to, numerous types of infections, aspergillosis (fever, cough, chest pain or breathlessness), meningitis and meningo-encephalitis, histoplasmosis, pneumonia, respiratory damage, and headaches.

In other aspects, the microbe is an aquatic fungus. In these aspects, the aquatic fungus can be present in water systems where water can be consumed or come into contact with humans or animals. Examples of aquatic fungi include, but are no limited to, *Absidia corymbifera, Absidia ramosa* (synonym for *Absidia corymbifera*), *Acremonium falciforme, Acremonium kiliense, Acremonium recifei, Ajellomyces capsulatus* (sexual form of *Histoplasma*), *Ajellomyces dermatitidis* (sexual form of *Blastomyces dermatitidis*), *Arthrographis cuboidea, Arthrographis kalrae, Aspergillus clavatus, Aspergillus flavus, Aspergillus fumigatus, Aspergillus glaucus* group, *Aspergillus nidulans, Aspergillus niger, Aspergillus oryzae, Aspergillus terreus* group, *Aspergillus ustus, Basidiobolus ranarum, Bipolaris, Blastomyces dermatitidis, Blastoschizomyces capitatus, Blastoschizomyces pseudotrichosporon* (synonym for *Blastoschizomyces capitatus*), *Candida albicans, Candida dubliniensis, Candida glabrata, Candida krusei, Candida lipolytica, Candida lusitaniae, Candida parapsilosis, Candida tropicalis, Cladophialophora bantiana, Cladophialophora carrionii, Coccidioides immitis, Conidiobolus coronatus, Coniothyrium fuckelii, Cryptococcus norformans, Curvularia, Epidermophyton floccosum, Exophiala castellanii, Exophiala dopicola, Exophiala jeanselmei, Exophila pisciphila, Exophiala salmonis, Exophiala spinifera, Exserohilum, Filobasidiella neoformans* (sexual form of *Cryptococcus norformans*), *Fonsecaea compacta, Fonsecaea pedrosoi, Fusarium oxysporum, Fusarium solani, Geotrichum candidum, Geotrichum capitatum* (synonym for *Blastoschizomyces capitatus*), *Geotrichum penicillatum, Histoplasma capsulatum* var. *capsulatum, Histoplasma capsulatum* var. *duboisii, Hortaea werneckii, Lacazia loboi, Lasiodiplodia theobromae, Leptosphaeria senegalensis, Madurella grisea, Madurella mycetomatis, Malassezia furfur, Microsporum audouinii, Microsporum canis, Microsporum distortum, Microsporum gallinae, Microsporum gypseum, Microsporum nanum, Mucor corymbifer* (synonym for *Absidia corymbifera*), *Nattrassia mangiferae, Neotestudina rosatii, Ochroconis gallo-* pava, *Onychocola Canadensis, Paracoccidioides brasiliensis, Phialophora parasitica, Phialophora repens, Phialophora verrucosa, Piedraia hortae, Pneumocystis carinii, Pseudallesheria boydii, Pyrenochaeta romeroi, Rhinocladiella aquaspersa, Rhinosporidium seeberi, Rhizomucor pusillus, Rhizopus arrhizus, Rhizopus oryzae, Rhodotorula glutinis, Rhodotorula minuta, Rhodotorula mucilaginosa, Saprolegnia parasitica, Scedosporium apiospermum, Scedosporium prolificans, Scopulariopsis brevicaulis, Scopulariopsis brumptii, Scopulariopsis candida, Scytalidium dimidiatum, Sporothrix schenckii, Trichophyton megninii, Trichophyton mentagrophytes, Trichophyton rubrum, Trichophyton schoenleinii, Trichophyton tonsurans, Trichophyton verrucosum, Trichosporon beigelii, Trichosporon capitatum* (synonym for *Blastoschizomyces capitatus*), or *Wangiella dermatitidis*.

In one aspect, the microbe is a pathogen to marine life (e.g., mammal, reptile, amphibian, fish, cephalopod, bivalve, monovalve, crustacean, or fish eggs). Examples include *Pfiesteria piscicida, Aphanomyces invadans, Ichthyophonus hoferi* (results in icthyophonus), or *Saprolegnia parasitica* (results in saprolegniasis), *Branchiomyces sanguinis* (results in bracnchiomycosis), or *Branchiomyces demigrans* (results in bracnchiomycosis).

In another aspect, the microbe is a crop pathogen from the genus *Fusarium, Ustilago, Alternaria*, or *Cochliobolus*. Examples of crop pathogens include, but are not limited to, *Colletorichum acutatum, C., gloeosporioides, Botryosphaeria parva, B. dothidea, Phomopsis sp., Fusarium oxysporum, Ustilago avenae, Ustilago esculenta, Ustilago maydis, Ustilago nuda, Ustilago tritici, Alternaria alternata, Alternaria arborescens, Alternaria arbusti, Alternaria blumeae, Alternaria brassicae, Alternaria brassicicola, Alternaria carotiincultae, Alternaria conjuncta, Alternaria dauci, Alternaria euphorbiicola, Alternaria gaisen, Alternaria infectoria, Alternaria japonica, Alternaria panax, Alternaria petroselini, Alternaria selini, Alternaria solani, Alternaria smyrnii, Cochliobolus carbonum, Cochliobolus heterostrophus, Cochliobolus lunatus*, or *Cochliobolus stenospilus*.

The microbe can also be a protozoan parasite. Examples of such parasites include, but are not limited to, *Ichthyophthirius multifiliis, Cryptocaryon irritans, Plasmodium falciparum, Plasmodium vivax, Giardia lamblia, Myxobolus cerebralis*, or *Cyclospora cayetanensis, Treponema pallidum, Trichomonas vaginalis*. In other aspects, the microbe is a parasitic worm such as a cestode, a nematode, or a trematode. Specific examples include, but are not limited to, a fluke, a whipworm, a hookworm, a pinworm, an ascarid, a filarid, a roundworm, a tapeworm. In the case of parasitic worms, the porphyrins can exhibit anti-helminthic activity and prevent diseases such as schistosomiasis or filariasis.

In other aspects, the microbe can be a spore. Examples of such spores include, but are not limited to, endospores, sporangiospores, zygospores, ascospores, basidiospores, aeciospores, urediospores: teliospores, oospores, carpospores, and tetraspores.

In another aspect, the microbe can be a collection of aggregated organisms in a biofilm. Biofilms typically form on living or non-living substrates. Biofilms are particularly relevant in hospitals and other biomedical applications, where certain biofilms can cause very debilitating diseases that are difficult to treat.

In certain aspects, the porphyrins described herein can be applied to a variety of different substrates where microbes can live and grow. For example, the porphyrins can be applied to an inert substrate (i.e., a substrate that is not a living organism). Examples of inert substrates include, but are not limited to, a recirculating cooling tower (e.g., electrical generating plants), an air conditioning system and coolers that recirculate water, a surgical or diagnostic instrument, an antiseptic wipe (e.g., hand wipes for personal use or to disinfect public shopping carts), a surface in a hospital or laboratory, a urinal, portable lavatory, a handwipe, a surface in a cell culture facility, a water sterilization system, the exterior of a watercraft (e.g., barge, boat, ship, sailboat, hovercraft), an exterior or interior wall of a domestic or commercial building, (e.g., piers, wharfs, etc.), or a wall or other substrate that is contaminated with a microbe that can be treated with the porphyrin to reduce the risk of inhaling the microbe. In other aspects, the porphyrin can be sprayed on military equipment and clothing in order to kill or prevent biological threats such as bacteria and viruses.

In other aspects, the substrate can be an agricultural product. For example, the porphyrins can be applied to crops (e.g., kiwi, avocado, grapes, bananas) and the supporting soil to prevent damage. In other aspects, the porphyrin can be applied to a fruit or vegetable after harvesting to prevent dangerous microbes from growing on the fruit or vegetable or kill existing organisms on the fruit or vegetable.

In one aspect, the substrate can be a living subject. For example, the porphyrins described herein can be applied directly to a mammal, bird, marsupial, reptile, amphibian, fish, cephalopod, bivalve, monovalve, crustacean, a beneficial insect, a beneficial arthropod, or fish eggs. In general, animals are vulnerable to a variety of microbes that produce debilitating diseases. The porphyrins described herein have a number of veterinary applications. For example, the porphyrins can be applied to the hoof of an ungulate such as an equine, ovine, bovine, or porcine to treat infections.

In one aspect, the porphyrins can be used in biomedical applications. For example, the substrate can be the skin of a subject. Infections caused by the introduction of bacteria and other microbes present on skin into the subject are a common and potentially serious problem. This is especially true in hospitals and other healthcare facilities. For example, when a patient is administered an IV, bacteria present on the skin are introduced into the patient. This is referred to as a line site infection. Although some disinfectants are effective, many have drawbacks. For example, numerous antibacterials have been either overused or misused, which leads to bacterial resistance against those particular antibacterials. This resistance has proven especially problematic in hospitals where numerous strains of multidrug resistant bacteria have been discovered over the past two decades.

The porphyrins having the formula I can be applied to or incorporated in a number of different articles that will ultimately come into contact with the skin. For example, the article can be a washcloth, bandage, medical tape, antiseptic wipe, handwipe, or sponge that has been contacted with the porphyrin. In certain aspects, the washcloths described herein are single use disposable items. In other aspects, the washcloths are reusable. In certain aspects, the washcloths described herein are similar to disposable alcohol or betadine containing swabs or wipes. In this aspect, the washcloth can be made of natural or artificial materials. For example, in one aspect, the wash cloth can be cotton. In another aspect, the wash cloth can be made of polyester.

The porphyrins can be applied to the articles using a variety of techniques. In one aspect, the articles can be sprayed with a solution of the porphyrin, while in other aspects, the articles can be dipped into a solution of the porphyrin. In certain aspects, when the article is a bandage or medical tape, the bandage or medical tape can be composed of a material that permits light to pass through the bandage or medical tape and contact the skin. As will be discussed below, light can pass though the material and activate the porphyrin.

In other aspects, the porphyrin can be applied to an article that is intended to be injected into the skin. For example, needles and lancets used in venipunctures, IV lines, and picc lines can be coated or impregnated with the porphyrin prior to injection so that upon penetration of the skin, microbial agents present on the skin are killed and are not incorporated in the skin.

In other aspects, the porphyrins described herein can be used in topical compositions. Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

It will be appreciated that the actual preferred amounts of porphyrin present on the articles or in the compositions described herein can vary according to the specific porphyrin being utilized, the particular articles or compositions used, the mode of application, and the particular region of the subject being treated. The articles and compositions described herein can be used in combination with additional disinfectants. For example, the articles and compositions can include a second disinfectant such as, for example, chlorhexidine, betadine (povidone-iodine), benzoin, isopropyl alcohol, ethyl alcohol, or any combination thereof.

The articles, compositions, and methods described herein can be used to prevent a skin infection from developing or treat an existing skin infection. The term "prevent" as used in this aspect ranges from a reduction in the growth rate of a microbe to the complete cessation of the microbe that can cause an infection. In certain aspects, the articles and compositions described herein can kill up to 100% of the microbes. If a skin infection is already present, the articles and compositions described herein can reduce the spread and symptoms of the infection (i.e., treat the infection) by killing the microbes responsible for the infection. The term "disinfect" as used herein with respect to skin applications includes the prevention and/or treatment of a skin infection.

Microbes such as bacterium and fungi can produce a variety of different symptoms and diseases. For example, numerous types of skin infections including line site infections, aspergillosis (fever, cough, chest pain or breathlessness), meningitis and meningo-encephalitis, histoplasmosis, pneumonia, respiratory damage, and headaches can be treated or prevented by the articles, compositions, and methods described herein. The articles, compositions, and methods described herein can kill or prevent the growth of these organisms.

The articles and compositions can be applied to any exposed surface of skin. The term "skin" includes any exposed surface on the subject that may be susceptible to infection caused by the microbes. For example, exposed mucosal membranes such as, for example, the vagina, the rectum, and the inter-lining of the nose can be contacted with the articles and compositions described herein. In one aspect, the articles and compositions described herein can be applied to the arms, legs, hands, feet, torso, or the head in order to disinfect this region of the subject. For example, the articles or compositions can be applied to the skin of a subject before and/or after the skin has been punctured (e.g., IV, picc line, lancet, etc.). Thus, the articles and compositions described herein are useful in the prevention or treatment of line site infections. In other aspects, the articles and compositions described herein can prevent or treat an infection of a wound present on the skin of a subject. For example, a wipe or bandage can be applied to an open wound (e.g., a cut or laceration on the skin) in order to disinfect the wound.

In other aspects, the porphyrins can kill or prevent the growth of microbes in aquatic environments including fresh and saltwater applications. For example, the porphyrins can be added to raceways, ponds, aquariums and other storage systems that hold aquatic organisms (e.g., fish, mammals, etc.).

In one aspect, the porphyrins can be used treat municipal water supplies and pools. For example, the porphyrins described herein are useful in killing or preventing the growth of the bacterium *Cryptosporidium*. In other aspects, the porphyrins can be used in back-country water purification to quickly and effectively kill *Giardia* and other health threats in lake and river waters. In one aspect, the porphyrins can be used to prevent the growth of disease vectors (e.g., killing mosquito larvae in standing water in tropical countries).

In another aspect, a method for killing or preventing the growth of a microbe using (a) contacting the microbe with a porphyrin having the structure I, wherein $R^1$-$R^4$ is a $C_1$ to $C_{14}$ alkyl group, and $X^-$ is an anion, and (b) exposing the porphyrin to light. In certain aspects, the porphyrin can be stable in the dark. Upon exposure to light, they are photosensitizers. In the presence of oxygen, the porphyrin upon exposure to light produces singlet oxygen that can react with an electron-rich substrate. Thus, when the porphyrin comes into contact with the microbe followed by exposure to light, the microbe is rendered inactive by singlet oxygen. The intensity and duration of the light can vary depending upon the amount of porphyrin used and the type of microbe that is targeted. For example, when the light is derived from an artificial light source, the light has an intensity of at least 5 mW/cm$^2$, or from 5 mW/cm$^2$ to 500 mW/cm$^2$. In this aspect, the duration of light exposure is from 1 second to 2 hours. Alternatively, the light source can be sunlight. The porphyrins described herein can absorb all visible wavelengths of sunlight, with the strongest absorption in the blue region. In other aspects, the porphyrins can be activated in the absence of light.

The porphyrins described herein can be formulated into a variety of different compositions depending upon the end-use of the porphyrins. For example, the porphyrins can be formulated into paints to prevent the formation of mold. In other aspects, as described above, the porphyrins can be formulated into topical compositions that can be easily applied to a body part of the subject (human or animal). Alternatively, the porphyrin can be formulated into solutions (e.g., aqueous based) that can be readily sprayed onto a substrate.

It is understood that any given particular aspect of the disclosed compositions and methods can be easily compared to the specific examples and embodiments disclosed herein, including the non-polysaccharide based reagents discussed in the Examples. By performing such a comparison, the relative efficacy of each particular embodiment can be easily determined. Particularly preferred compositions and methods are disclosed in the Examples herein, and it is understood that these compositions and methods, while not necessarily limiting, can be performed with any of the compositions and methods disclosed herein.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Chemicals.

TMP ($R^1$-$R^4$=Me; X=tosylate) and lauryl methyl pyrifrin (LMP), $R^1$=$C_{12}$ linear alkyl; $R^2$-$R^4$=Me; X=tosylate) were obtained from Frontier Scientific, Inc. (Logan, Utah); Medium (DMEM with L-Glu, FBS, Pen/Strep, EMEM w/Earl's salts, and Basal medium in Earle's BSS) were bought from American Type Culture Collection (ATCC). EpiLife medium was purchased from Invitrogen (Madison, Wis.).

Cells.

Human neonatal epidermal keratinocytes (HEKn) were obtained from Invitrogen (Madison, Wis.).

Dark Cytotoxicity.

HEKn cells of type (100,000) were seeded in 6-well plastic plates with 2 ml of complete medium for each cell type. After 24 h, the medium was replaced with increasing concentration of porphyrins (0-300 μM) and incubated for another 24 h (2). At the end of the incubation period the cells were washed with PBS, removed from the dishes by exposure to trypsin and stained with trypan blue for determination of cell survival. The survival of cells was normalized to percentage of viable cells of control samples (untreated).

Phototoxicity.

HEKn cells were prepared as described above for the dark cytotoxicity assay with the same porphyrins treatment. Immediately after the exposure to the porphyrins, the cells were exposed for 2 h to ambient fluorescent room light, and then returned to the incubator. After 24 h the trypan blue exclusion test was applied and the survival of the irradiated cells was evaluated relative to cell samples that were neither incubated with porphyrin nor irradiated.

Skin Irritation Test in Mice.

Lauryl methyl pyrifrin and TMP, two synthesized meso-substituted cationic porphyrins, were tested in vivo to determine the dermal irritation potential to the skin of the mice. The two test agents were prepared with three different concentrations individually, 3 μM, 30 μM, and 300 μM. 10% formic acid and PBS were used as positive and negative control respectively (n=6). Balb/c mice, which had not been used in previous experiments and were observed to be free from any skin irritation, trauma, or adverse clinical signs prior to initiation of the studies, were randomized and grouped for designed test conditions. The back of the animals were clipped free of fur with an electric clipper at least 4 hours before application of the sample. Prior to the application of test agents, each mouse received four parallel epidermal abrasions with a sterile needle at one side of the test area while the skin at the opposite side remained intact. Under anesthesia condition, a 0.5 ml sample of the test article was then applied to each mouse by introduction under a double gauze layer to an area of skin approximately 1"×1" (2.54×2.54 cm) square. The patches were backed with plastic, covered with a non reactive tape and the entire test site wrapped with a binder. Animals will be returned to their cages. After a 24 hr exposure, the binders were removed and the skin wiped to remove any test substance still remaining Animals were observed for signs of erythema and edema at 24 and 72 hours after test substance application and scored according to the FHSA-recommended Draize Scoring Criteria Table 1). The Primary Irritation Index (P.I.I.) (sum of the scored reactions divided by 24 (two scoring intervals multiplied by two test parameters multiplied by six mice)) of the test article was calculated following test completion. A material producing a P.I.I. score of greater than or equal to 5.00 would be considered positive; the material would be considered a primary irritant to the skin (Table 2).

TABLE 1

DRAIZE[1] EVALUATION OF DERMAL REACTIONS

| SKIN REACTIONS | SCORE |
| --- | --- |
| Erythema and Eschar Formation (Most severely affected area graded): | |
| No erythema | 0 |
| Very slight erythema (barely perceptible) | 1 |
| Well-defined erythema | 2 |
| Moderate to severe erythema | 3 |
| Severe erythema (beet redness) to slight eschar formation (injuries in depth) | 4 |
| Edema Formation (Most severely affected area graded): | |
| No edema | 0 |
| Very slight edema (barely perceptible) | 1 |
| Slight edema (edges of area well defined by definite raising) | 2 |
| Moderate edema (raising approximately 1 millimeter) | 3 |
| Severe edema (raised more than 1 mm and extending beyond the area of exposure) | 4 |

NOTE:
Test sites assigned a "4" score for erythema require further description as to the extend of tissue injury.
[1]Draize, J. H. 1959. Dermal Toxicity. Pages 46-59 in Appraisal of the Safety of Chemicals in Food, Drugs and Cosmetics. The Association of Food and Drug Officials of the United States, Bureau of Food and Drugs, Austin, TX.

TABLE 2

EVALUATION OF PRIMARY IRRITATION INDEX

| INDEX | EVALUATION |
| --- | --- |
| 0.00 | No irritation |
| 0.04-0.99 | Irritation barely perceptible |
| 1.00-1.99 | Slight Irritation |
| 2.00-2.99 | Mild Irritation |
| 3.00-5.99 | Moderate Irritation |
| 6.00-8.00 | Severe Irritation |

Results

Cytotoxicity of Porphyrins Toward Different Cell Types.

The phototoxicity of porphyrin derivatives lauryl methyl pyrifrin and TMP were evaluated in HEKn cells. The compounds were found to be nontoxic or slightly toxic to the cells in the dark (>60% survival rate), up to 300 μM concentration. Upon exposure to visible light, the porphyrins showed cytotoxicity to all cell types, with cell survival rates below 20% at the highest concentration studied.

Skin Irritation Test in Mice.

Figure 3:
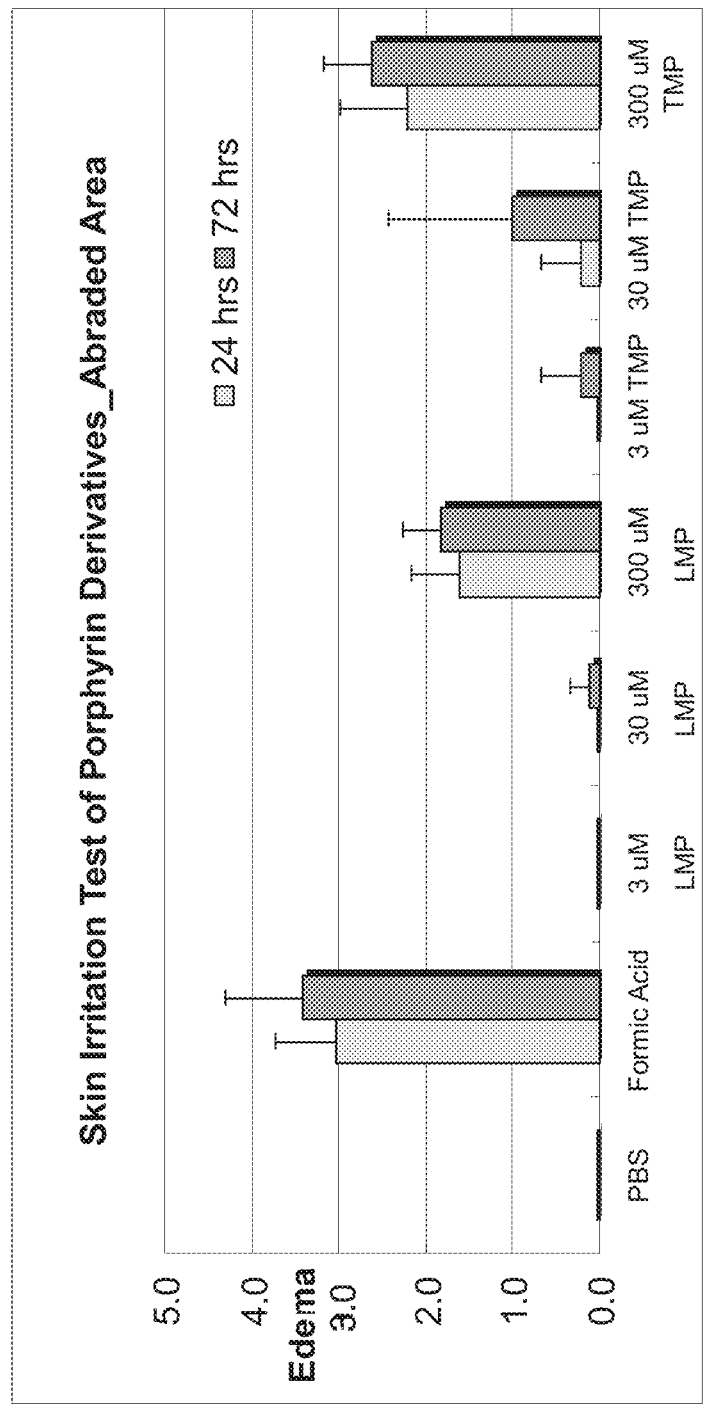
FIG. 3 shows erythema scoring of lauryl methyl pyrifrin (LMP) and TMP porphyrin in an intact area of mice.
Figure 4:
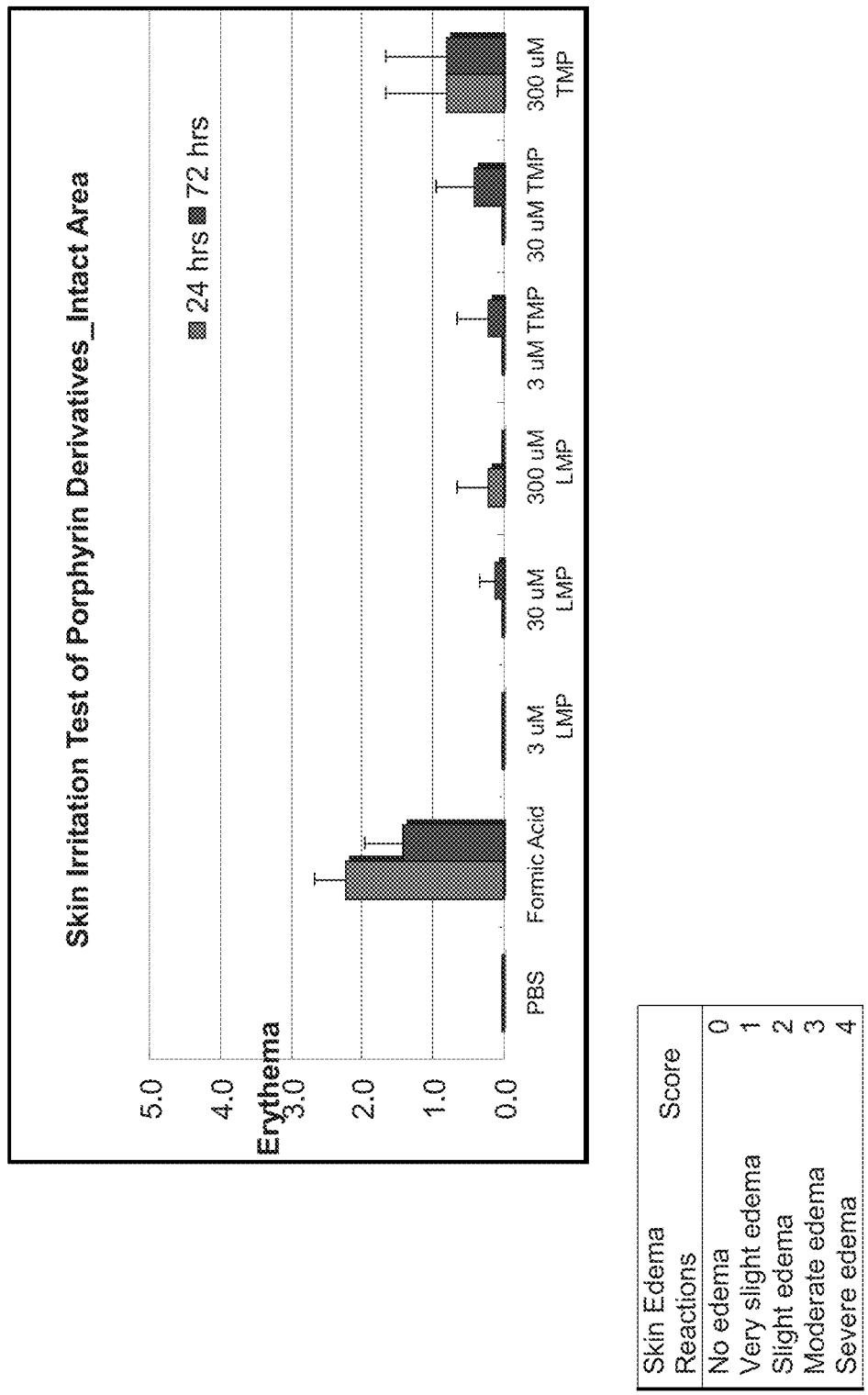
FIG. 4 shows edema scoring of lauryl methyl pyrifrin (LMP) and TMP porphyrin in an abraded area of mice.
Figure 5:
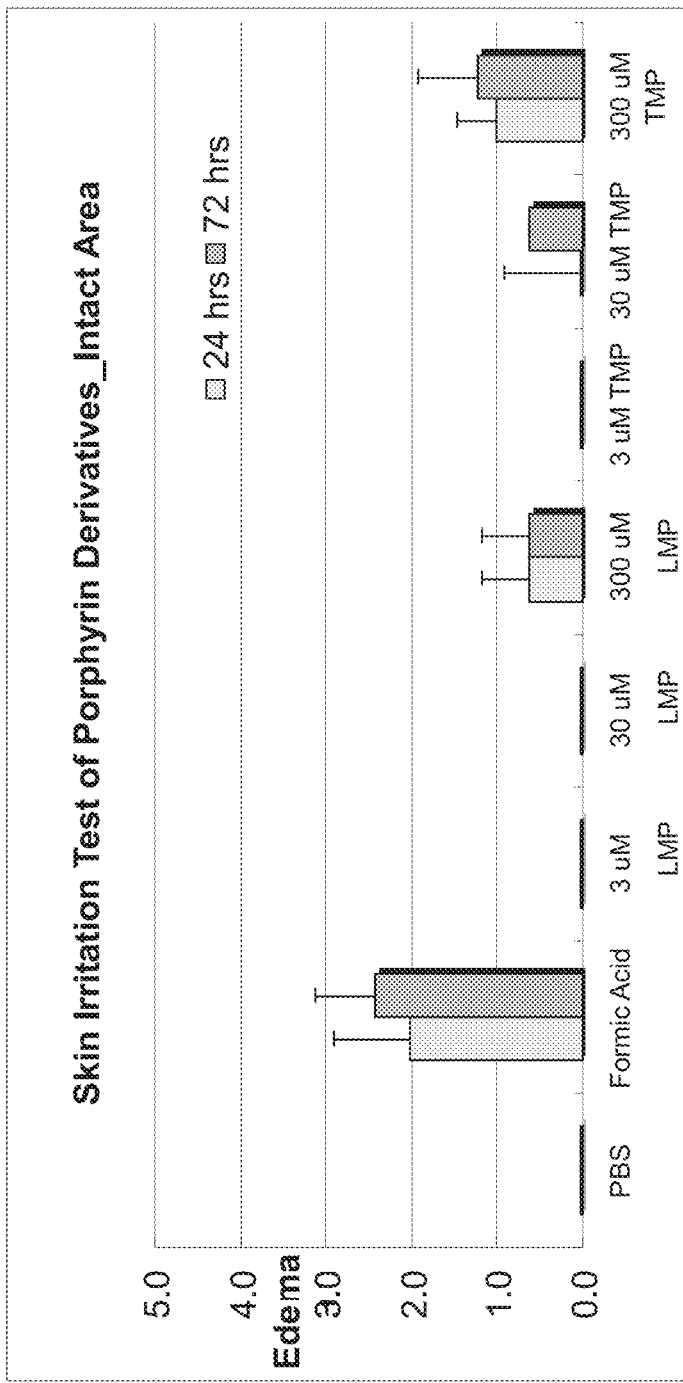
FIG. 5 shows edema scoring of lauryl methyl pyrifrin (LMP) and TMP porphyrin in an intact area of mice.

Gross pictures of mice in different treatment groups were represented in FIG. 1. Individual results of dermal scoring were expressed by erythema for abraded area (FIG. 2); intact area (FIG. 3); edema for abraded area (FIG. 4); and intact area (FIG. 5). After 24 hours, very slight erythema was observed on most of 300 μM lauryl methyl pyrifrin (6/6), 30 μM (4/6) TMP and 300 μM TMP (5/6), and 30 μM lauryl methyl pyrifrin (2/6), with well defined erythema on 300 μM TMP (6/6). Slight edema was observed on both 300 μM lauryl methyl pyrifrin and 300 μM TMP treatment mice. After 72 hours, very slight erythema was observed on 30 μM lauryl methyl pyrifrin treatment, slight difference was observed from other treatment groups. At the intact area, no erythema and edema were observed on all the lauryl methyl pyrifrin and TMP, except for 300 μM TMP with very slight erythema and edema. The primary irritation index of 3 μM lauryl methyl pyrifrin was calculated to be 0.00, 0.175 for 30 μM lauryl methyl pyrifrin, 1.4 for 300 μM lauryl methyl pyrifrin, 0.6 for 3 μM TMP, 1.1 for 30 μM TMP, and 2.9 for 300 μM TMP. Therefore, 3 μM lauryl methyl pyrifrin has no irritation effect on skin at all; 30 μM lauryl methyl pyrifrin and 3 μM TMP have irritation barely perceptible; 300 μM lauryl methyl pyrifrin and 30 μM TMP have slight irritation; 300 μM TMP can be considered to have mild irritation.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A topical composition comprising a pharmaceutical carrier and a porphyrin of the formula I

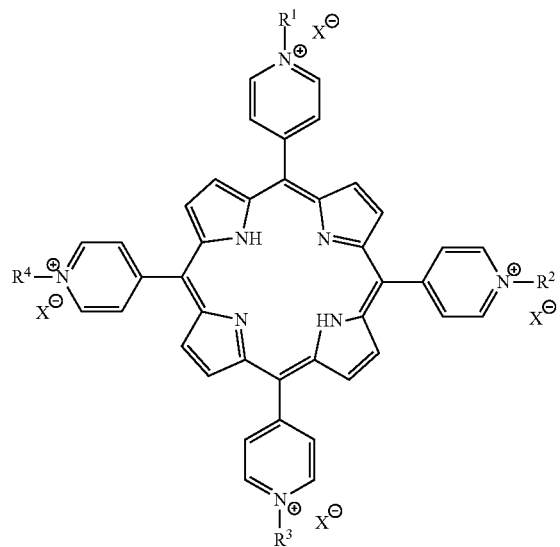

wherein $R^1$ is a $C_{12}$ straight chain alkyl group;
$R^2$-$R^4$ are each a methyl group; and
$X^-$ is an anion.

2. The composition of claim 1, wherein X is a halide, sulfate, acetate, lactate, nitrate, phosphate, carbonate, bicarbonate, or tosylate.
3. The composition of claim 1, wherein the pharmaceutical carrier is a powder.
4. The composition of claim 1, wherein the pharmaceutical carrier is an ointment.
5. The composition of claim 1, wherein the pharmaceutical carrier is a cream.
6. The composition of claim 1, wherein the pharmaceutical carrier is a gel.
7. The composition of claim 1, wherein the pharmaceutical carrier is a spray.
8. An article comprising a porphyrin of the formula I

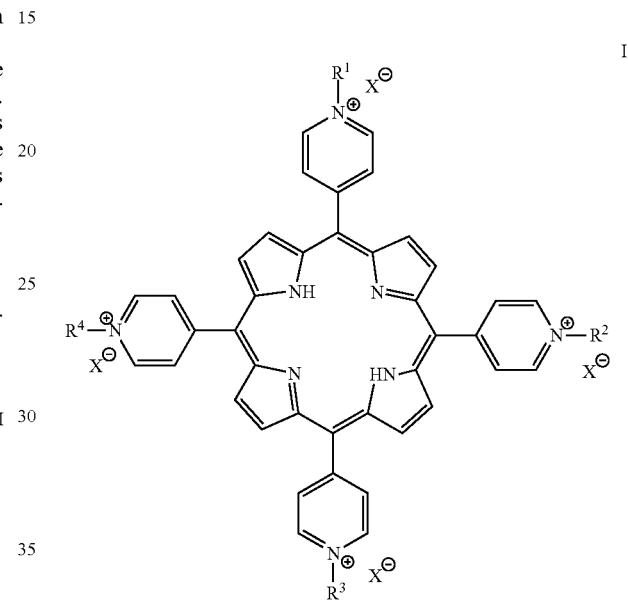

wherein $R^1$ is a $C_{12}$ straight chain alkyl group;
$R^2$-$R^4$ are each a methyl group; and
$X^-$ is an anion.
9. The article of claim 1, wherein X is a halide, sulfate, acetate, lactate, nitrate, phosphate, carbonate, bicarbonate, or tosylate.
10. The article of claim 8, wherein the article comprises a washcloth, a bandage, an antiseptic wipe, a handwipe, a sponge, a lancet, a medical tape, or a picc line.
11. The article of claim 8, wherein when the article comprises a material that permits light to pass through the article.
12. The article of claim 8, wherein the article further comprises a second disinfectant.
13. The article of claim 12, wherein the second disinfectant comprises chlorhexidine, betadine, benzoin, isopropyl alcohol, ethyl alcohol, or any combination thereof.

* * * * *